(12) United States Patent
Felber et al.

(10) Patent No.: US 11,744,954 B2
(45) Date of Patent: Sep. 5, 2023

(54) COLLECTION OF INJECTION DEVICE DATA USING ENERGY HARVESTED FROM AN EXTERNAL DEVICE

(71) Applicant: SANOFI, Paris (FR)

(72) Inventors: Matthias Felber, Winterthur (CH); Nathanael Wettstein, Seuzach (CH); Philipe Just, Wil (CH); Felix Kramer, Wil (CH)

(73) Assignee: Sanofi, Paris (FR)

( * ) Notice: Subject to any disclaimer, the term of this patent is extended or adjusted under 35 U.S.C. 154(b) by 633 days.

(21) Appl. No.: 16/954,460

(22) PCT Filed: Dec. 18, 2018

(86) PCT No.: PCT/EP2018/085392
§ 371 (c)(1),
(2) Date: Jun. 16, 2020

(87) PCT Pub. No.: WO2019/121613
PCT Pub. Date: Jun. 27, 2019

(65) Prior Publication Data
US 2021/0069425 A1   Mar. 11, 2021

(30) Foreign Application Priority Data
Dec. 21, 2017   (EP) .................... 17306868

(51) Int. Cl.
*A61M 5/315*   (2006.01)
*G16H 20/17*   (2018.01)
(Continued)

(52) U.S. Cl.
CPC ...... *A61M 5/31568* (2013.01); *A61M 5/3146* (2013.01); *G06K 7/10158* (2013.01);
(Continued)

(58) Field of Classification Search
CPC .... A61M 5/20; A61M 5/31568; A61M 5/002; A61M 5/14248; A61M 5/31511; A61M 5/2033; A61M 5/24; G16H 20/17
See application file for complete search history.

(56) References Cited

U.S. PATENT DOCUMENTS 7,359,753 B2   4/2008   Bange et al.
9,020,456 B2   4/2015   Wentzloff et al.
(Continued)

FOREIGN PATENT DOCUMENTS

JP   2014-507922   3/2014
JP   2017-529918   10/2017
(Continued)

OTHER PUBLICATIONS

PCT International Preliminary Report on Patentability in International Appln. No. PCT/EP2018/085392, dated Jun. 23, 2020, 7 pages.

(Continued)

*Primary Examiner* — Manuel A Mendez
(74) *Attorney, Agent, or Firm* — Fish & Richardson P.C.

(57) ABSTRACT

Implementations of the present disclosure are directed to conserving energy of an injection device by using a sensor attached to the housing, the sensor configured to detect a signal associated with an amount of medicament within the injection device and to generate a sensor signal based on the signal, a control component coupled to the sensor, the control component configured to harvest energy to process the sensor signal and to generate injection device data, and an antenna coupled to the control component and configured to transmit a radio frequency signal based on the injection device data.

20 Claims, 4 Drawing Sheets

(51) Int. Cl.
G16H 40/67 (2018.01)
A61M 5/31 (2006.01)
G06K 7/10 (2006.01)
G06K 19/07 (2006.01)

(52) U.S. Cl.
CPC ......... *G06K 19/0709* (2013.01); *G16H 20/17* (2018.01); *G16H 40/67* (2018.01); *A61M 2005/3126* (2013.01); *A61M 2205/3327* (2013.01); *A61M 2205/3368* (2013.01); *A61M 2205/3382* (2013.01); *A61M 2205/3592* (2013.01); *A61M 2205/502* (2013.01); *A61M 2205/581* (2013.01); *A61M 2205/587* (2013.01); *A61M 2205/8206* (2013.01); *A61M 2205/8237* (2013.01)

(56) References Cited

U.S. PATENT DOCUMENTS

| | | |
|---|---|---|
| 9,292,301 B1 | 3/2016 | Calhoun et al. |
| 9,764,083 B1 | 9/2017 | Savoie et al. |
| 2008/0091139 A1 | 4/2008 | Srinivasan et al. |
| 2012/0176609 A1 | 7/2012 | Seppa et al. |
| 2013/0331051 A1 | 12/2013 | Wentzloff et al. |
| 2014/0269563 A1 | 9/2014 | Wentzloff et al. |
| 2015/0087255 A1 | 3/2015 | Wentzloff et al. |
| 2015/0303975 A1 | 10/2015 | Calhoun et al. |
| 2015/0382296 A1 | 12/2015 | Wentzloff et al. |
| 2016/0037486 A1 | 2/2016 | Wentzloff et al. |
| 2017/0274149 A1 | 9/2017 | Aeschlimann |
| 2017/0354326 A1 | 12/2017 | Pugh et al. |

FOREIGN PATENT DOCUMENTS

| | | |
|---|---|---|
| JP | 2017-219847 | 12/2017 |
| WO | WO 2012/092209 | 7/2012 |
| WO | WO 2014/085857 | 6/2014 |
| WO | WO 2016/038498 | 3/2016 |
| WO | WO 2016/162298 | 10/2016 |

OTHER PUBLICATIONS

PCT International Search Report and Written Opinion in International Appln. No. PCT/EP2018/085392, dated Apr. 8, 2019, 10 pages.
Itoh, "Ultra low power wireless sensor nodes for expanding application of the Internet of Things," 2016 IEEE CPMT Symposium Japan (ICSJ), Nov. 7, 2016, 2 pages.
Abdolvand et al., "Passive Wireless Sensor System Utilizes Piezoelectric MEMS Resonator", University of Central Florida, Jun. 2015, 2 pages.
Adhikari, "Understanding Millimeter Wave Wireless Communication", Loea Corporation, 2008, 7 pages.
Amadjikpe et al., "Proximity Effects of Plastic Laptop Covers on Radiation Characteristics of 60-GHz Antennas", IEEE Antennas and Wireless Propagation Letters, Jun. 2009, 8:763-766.
Bae et al., "RF Wakeup Sensor for Wireless Sensor Networks", International Journal of Multimedia and Ubiquitous Engineering, May 2012, 7(2): 433-438.
Bhattacharyya et al., "Towards SCARS: A Chip-less RFID Sensor for Pervasive Surface Crack Detection", RFID-Technologies and Applications (RFID-TA), IEEE International Conference, 2012, 6 pages.
Calhoun et al., "Static Noise Margin Variation for Sub-threshold SRAM in 65-nm CMOS", IEEE Journal of Solid-State Circuits, Jul. 2006, 41(7): 1673-1679.
Chen et al., "A cubic-millimeter energy-autonomous wireless intraocular pressure monitor", 2011 IEEE International Solid-State Circuits Conference, Feb. 2011, pp. 310-312.
Collonge et al., "Influence of the Human Activity on Wide-Band Characteristics of the 60 GHz Indoor Radio Channel", IEEE Transactions on Wireless Communications, Dec. 2004, 3(6):2396-2406.
Crepaldi et al., "A Very Low-Complexity 0.3-4.4 GHz 0.004 mm2 All-Digital Ultra-Wide-Band Pulsed Transmitter for Energy Detection Receivers", IEEE Transactions on Circuits and Systems 1: Regular Papers, Oct. 2012, 59(10): 2443-2455.
developer.android.com [online], "AudioEffect", Dec. 2010, retrieved on Mar. 8, 2021, retrieved from URL <"https://developer.android.com/reference/android/media/audiofx/AudioEffect.html">, 26 pages.
Doclo et al., "DSP in Hearing Aids and Cochlear Implants", EURASIP Journal on Applied Signal Processing, Nov. 2005, 18:2911-2914.
Electronic Communications Committee, ""ECC Decision of Dec. 1, 2006 on the harmonized conditions for devices using Ultra-Wideband (UWB) technology with Low Duty Cycle (LDC) in the frequency band 3.4-4.8 GHz"", ECC, Dec. 1, 2006, 4 pages.
Elhawil et al., "A Quasi-Optical Free-Space Method for Dielectric Constant Characterization of Polymer Materials in mm-wave Band", Proceedings of 12th Annual Symposium of the IEEE, Dec. 2007, pp. 187-190.
everspin.com [online], "MRAM Replaces FRAM (FeRAM)", 2015, retrieved on Mar. 8, 2021, retrieved from URL <"https://www.everspin.com/mram-replaces-fram-feram">, 2 pages.
Federal Communications Commission, "Allocations and Service Rules for The 71-76 GHz, 81-86 GHz, and 92-95 GHz Bands", Memorandum Opinion and Order, Mar. 2005, 39 pages.
Federal Communications Commission, "Part 15 Rules for Unlicensed Operation in the 57-64 GHz Band", Report and Order, Aug. 2013, 32 pages.
Federal Communications Commission, "Revision of Part 15 of the Commission's Rules Regarding Ultra WideBand Transmission Systems", Report and Order, Apr. 2002, 118 pages.
Garcia et al., "60 GHz time-variant shadowing characterization within an Airbus 340", IEEE Proceedings of the Fourth European Conference on Antennas and Propagation, Apr. 2010, pp. 1-5.
Genovesi et al., "D2.2—State of the art of materials sensitive to environmental variables report", Emergent, Jan. 2015, 30 pages.
Graves et al., "A Novel Connectionist System for Unconstrained Handwriting Recognition", IEEE Transactions on Pattern Analysis and Machine Intelligence, May 2009, 31(5): 855-868.
Gustafson et al., "Characterization of 60 GHz Shadowing by Human Bodies and Simple Phantoms", Radioengineering, 21(4): 979-984.
Gustafson, "60 GHz Wireless Propagation Channels: Characterization, Modeling and Evaluation", Thesis for the Degree of Doctor of Science, Lund University, 2014, 245 pages.
Hao et al., "iSleep: unobtrusive sleep quality monitoring using smartphones", Proceedings of the 11th ACM Conference on Embedded Networked Sensor Systems, Nov. 2013, 14 pages.
Harris, "Absorption of Sound in Air versus Humidity and Temperature", The Journal of the Acoustical Society of America, 1966, 40(1):148-159.
ibm.com [online], "Made in IBM Labs: IBM Scientists Unveil Highly Integrated Millimeter-Wave Transceiver for Mobile Communications and Radar Imaging applications", Jun. 4, 2013, retrieved on Mar. 9, 2021, retrieved from URL <"https://www-03.ibm.com/press/us/en/pressrelease/41225.wss">, 3 pages.
Islam et al., "On a compact printable dual-polarized chipless RFID tag using slot length variation encoding technique for barcode replacement", IEEE MTT-S International Microwave Symposium, May 2015, 4 pages.
Jinsong, "On Passive Wireless Sensors Based on Intermodulation Communication", Doctoral Dissertation for the Degree of Doctor of Science (Technology), Aalto University, Department of Radio Science and Engineering, Oct. 2015, 85 pages.
Klaric et al., "Single-Chip Millimeter Wave Radar", Microwave Journal, Jan. 2015, 10 pages.
Kokkinakis et al., "Single and Multiple Microphone Noise Reduction Strategies in Cochlear Implants", Trends in Amplification, 2012, 16(2): 102-116.
Laila et al., "A Novel Polarization Independent Chipless RFID Tag Using Multiple Resonators", Progress in Electromagnetics Research Letters, 2015, 55: 61-66.

(56) References Cited

OTHER PUBLICATIONS

Li et al., "Surface Acoustic Wave Based Magnetic Sensors", Modeling and Measurement Methods for Acoustic Waves and for Acoustic Micro-devices, 2013, pp. 354-380.
Lu et al., "StressSense: Detecting Stress in Unconstrained Acoustic Environments using Smartphones", Proceedings of the 2012 ACM Conference on Ubiquitous Computing, Sep. 2012, pp. 351-360.
Marcus et al., "Report of the Unlicensed Devices and Experimental Licenses Working Group", Federal Communications Commission Spectrum Policy Task Force, Nov. 15, 2002, 24 pages.
Meena et al., "Overview of emerging nonvolatile memory technologies", Nanoscale Research Letters, Sep. 2014, 9:526, 33 pages.
Melik et al., "Metamaterial based telemetric strain sensing in different materials", Optics Express, Feb. 2010, 18(5): 5000-5007.
Mercier et al., "Ultra-low-power UWB for sensor network applications", IEEE International Symposium on Circuits and Systems, Jun. 2008, pp. 2562-2565.
Merz, "Analysis of Low Power, Low Data Rate Ultra Wideband Impulse Radio System", Thesis for the Degree of Doctor of Science, Universite De Neuchatel, Institut de Microtechnique, Feb. 2009, 206 pages.
Mohl et al., "The mono-pulsed nature of sperm whale clicks", The Journal of the Acoustical Society of America, Jul. 2003, 114(2): 1143-1154.
Myers et al. "A Subthreshold ARM Cortex-M0+ Subsystem in 65 nm CMOS for WSN Applications with 14 Power Domains, 10T SRAM, and Integrated Voltage Regulator", IEEE Journal of Solid-State Circuits, Jan. 2016, 51(1): 31-44.
Occhiuzzi et al., "Passive RFID Strain-Sensor Based on Meander-Line Antennas", IEEE Transactions on Antennas and Propagation, Dec. 2011, 59(12):4836-4840.
Ozbey et al., "Wireless Measurement of Elastic and Plastic Deformation by a Metamaterial-Based Sensor", Sensors, 2014, 14(10): 19609-19621.
Peterson, "Wireless Sensor Interrogator Design For Passive, Resonant Frequency Sensors Using Frequency Modulation Spectroscopy", Thesis for the Degree of Master of Science in Electrical Engineering, Montana State University, Apr. 2009, 123 pages.
Phan et al., "Giant magnetoimpedance materials: Fundamentals and applications", Progress in Materials Science, Feb. 2008, 53(2): 323-420.
Pletcher et al., "A 52 mu W Wake-Up Receiver With-72 dBm Sensitivity Using an Uncertain-IF Architecture", IEEE Journal of Solid-State Circuits, Feb. 2009, 44(1): 269-280.
Pletcher et al., "A 65µW, 1.9 GHz RF to Digital Baseband Wakeup Receiver for Wireless Sensor Nodes", IEEE Custom Integrated Circuits Conference, Oct. 2007, 539-542.
Pohl, "Passive Radio Sensor Systems", HABILITATIONSSCHRIFT, 2000, 120 pages.
Prenat et al., "Ultra-Fast and High-Reliability SOT-MRAM: From Cache Replacement to Normally-Off Computing", IEEE Transactions on Multi-Scale Computing Systems, Jan. 2016, 2(1): 49-60.
Quintero Diaz de Leon, "Analysis and Design of Ultra-Wideband Antennas in the Spectral and Temporal Domains", Thesis for the Degree of Doctor of Science, Ecole Polytechniue Federale de Lausanne, 2010, 141 pages.
Ramos et al., "Time-Domain Measurement of Time-Coded UWB Chipless RFID Tags", Progress in Electromagnetics Research, May 2011, 116: 313-331.
Roberts et al., "A 98nW Wake-up Radio for Wireless Body Area Networks", IFEE Radio Frequency Integrated Circuits Symposium, 2012, 4 pages.
Scott et al., "A Capacitively-Loaded MEMS Slot Element for Wireless Temperature Sensing of up to 300° C.", IEEE MTT-S International Microwave Symposium Digest, Jul. 2009, pp. 1161-1164.
Shao, "Fully Printed Chipless RFID Tags towards Item-Level Tracking Applications", Thesis for the degree of Doctor of Philosophy, Royal Institute of Technology, School of Information and Communication Technology, 2014, 95 pages.
Silver et al., "Mastering the game of Go with deep neural networks and tree search", Nature, Jan. 2016, 529(7587): 484-489.
Tabesh et al., "A power-harvesting pad-less mm-sized 24/60GHz passive radio with on-chip antennas", 2014 Symposium on VLSI Circuits Digest of Technical Papers, Jun. 2014, 2 pages.
Takahagi et al., "Low-power wake-up receiver with subthreshold CMOS circuits for wireless sensor networks", Analog Integrated Circuits and Signal Processing, Jul. 2012, 75(2): 199-205.
Towsey et al., "Technical report: acoustic analysis of the natural environment", Queensland University of Technology, 2011, 34 pages.
Umbdenstock et al., "Wake-Up-Receiver in energy efficient Wireless Sensor Networks for security applications", Proceedings of the 7th edition of the Interdisciplinary Workshop on Global Security, 2013, 4 pages.
Valenzise et al., "Scream and gunshot detection and localization for audio-surveillance systems", IEEE Conference on Advanced Video and Signal Based Surveillance, Oct. 2007, pp. 21-26.
Vaseghi et al., "Detection and suppression of impulsive noise in speech communication systems", IEE Proceedings I (Communications, Speech and Vision), 1990, 137(1): 38-46.
Viikari et al., "RFID MEMS sensor concept based on intermodulation distortion", IEEE Sensors Journal, Jan. 2010, 9(12): 1918-1923.
White et al., "WreckWatch: Automatic Traffic Accident Detection and Notification with Smartphones", Mobile Networks and Applications, Mar. 2011, 16: 285-303.

COLLECTION OF INJECTION DEVICE DATA USING ENERGY HARVESTED FROM AN EXTERNAL DEVICE

CROSS REFERENCE TO RELATED APPLICATIONS

The present application is the national stage entry of International Patent Application No. PCT/EP2018/085392, filed on Dec. 18, 2018, and claims priority to Application No. EP 17306868.5, filed on Dec. 21, 2017, the entire disclosures of which are incorporated herein by reference.

TECHNICAL FIELD

Electronic injection devices allow patients to safely administer a medicament, without the need for constant supervision by medical staff, while enabling transmission of treatment data to the medical staff.

BACKGROUND

Treatment data is generally transmitted by electronic components that are characterized by a "medium" or "typical" power consumption. Usually, electronic injection devices are powered by a battery integrated within the device or through wired connection by an external energy supply. Both integrated batteries and wired connections present several disadvantages. For example, current configurations of electronic injection devices lead to idle drainage of the energy supply, such that, even if the electronic injection device has not been used, long shelf life can exhaust the life of the battery. A low battery condition can lead to no- or malfunction of the device, an incorrect dosage, a missed dosage, or it can even make the electronic injection device unusable by stopping the operation of the electronic components.

SUMMARY

Implementations of the present disclosure include modules for attachment to injection devices, injection devices, and systems using an IoT platform chip for ultra-low RF communication. In accordance with one aspect of the present disclosure, a module for attachment to an injection device includes a housing configured to be attached to a surface of the injection device, a sensor attached to the housing, configured to detect a signal associated with an amount of medicament within the injection device and to generate a sensor signal based on the signal, a control component coupled to the sensor, configured to harvest energy to process the sensor signal and to generate injection device data, and an antenna coupled to the control component and configured to transmit a radio frequency (RF) signal based on the injection device data.

In some implementations, the module includes a transceiver configured to enable the transmission of the injection device data from the control component to the antenna. In some implementations, the control component includes an energy harvester configured to harvest energy from at least one of an interrogation signal and a priming operation of the injection device. In some implementations, the operation of the injection device includes a displacement of one of a push button, a plunger head and a plunger rod of the injection device. In some implementations, the control component includes a boost converter configured to increase a voltage level of an energy supplied by the energy harvester. In some implementations, the control component is configured to determine whether the harvested energy is sufficient to activate one or more additional components of the injection device. In some implementations, if it is determined that the harvested energy is not sufficient to activate the one or more additional components, the control component is configured to retrieve supplemental energy from at least one of a rechargeable battery, a capacitor, and an intermediate energy storage.

In some implementations, the module includes an integrated voltage regulator configured to regulate the voltage level generated by the boost converter. In some implementations, the sensor includes at least one of a temperature sensor, a humidity sensor, and a fill level sensor. In some implementations, the sensor is configured to generate the sensor signal using ultra-low power. In some implementations, the ultra-low power is in a range from about 50 nW to about 1 µW.

In accordance with another aspect of the present disclosure, an injection device includes: a sensor configured to detect a signal associated with an amount of medicament within the injection device and to generate a sensor signal based on the signal, a control component electrically coupled to the sensor, configured to harvest energy to process the sensor signal and to generate injection device data, and an antenna electrically coupled to the control component and configured to transmit a radio frequency (RF) signal based on the injection device data.

In some implementations, the injection device includes a transceiver configured to enable the transmission of the injection device data from the control component to the antenna. In some implementations, the control component includes an energy harvester configured to harvest energy from at least one of an interrogation signal and a priming operation of the injection device. In some implementations, the priming operation of the injection device includes a displacement of one of a push button and a piston of the injection device. In some implementations, the control component includes a boost converter configured to increase a voltage level of an energy supplied by the energy harvester. In some implementations, the injection device includes an integrated voltage regulator configured to regulate the voltage level generated by the boost converter. In some implementations, the sensor includes at least one of a temperature sensor, a humidity sensor, and a fill level sensor.

In accordance with another aspect of the present disclosure, a medicament injection system includes: an injection device and a computing device configured to receive a radio frequency (RF) signal transmitted by the injection device. The injection device includes: a sensor configured to detect a signal associated with an amount of medicament within the injection device and to generate a sensor signal based on the signal, a control component electrically coupled to the sensor, configured to harvest energy to process the sensor signal and to generate injection device data, and an antenna electrically coupled to the control component and configured to transmit the RF signal based on the injection device data.

In some implementations, the control component includes an energy harvester configured to harvest energy from at least one of an interrogation signal generated by the computing device and a priming operation of the injection device. In some implementations, the priming operation of the injection device includes a displacement of one of a push button and a piston of the injection device. In some implementations, the control component includes a boost converter configured to increase a voltage level of an energy supplied by the energy harvester.

It is appreciated that systems in accordance with the present disclosure can include any combination of the aspects and features described herein. That is to say that methods in accordance with the present disclosure are not limited to the combinations of aspects and features specifically described herein, but also include any combination of the aspects and features provided.

The details of one or more embodiments of the present disclosure are set forth in the accompanying drawings and the description below. Other features and advantages of the present disclosure will be apparent from the description and drawings, and from the claims.

BRIEF DESCRIPTION OF THE FIGURES

Like reference symbols in the various drawings indicate like elements.

DETAILED DESCRIPTION

Implementations of the present disclosure are generally directed to data collection using an Internet-of-Things (IoT) platform chip integrated into an injection device. The IoT platform chip is an ultra-low power (μW) platform chip, configured to process a signal received from a sensor of the injection device and to transmit injection device data using an antenna integrated in the injection device to another device within in an IoT network. The IoT network includes a variety of medical devices designed for performing medical treatment, monitoring medical treatment, and/or measuring patient physiological parameters, cameras recording or streaming live feeds of patient treatment, mobile devices with built-in sensors, and other devices that assist patients and healthcare providers during medical treatment operations. More particularly, implementations of the present disclosure are directed to a mechanism configured to harvest energy to power electronic components of the injection device to collect and transmit injection device data in the IoT network.

Electronic components of an electronic injection device may drain the device's energy source even when the device is idle. Accordingly, collection, processing and transmission of injection device data can be hindered by idle drained batteries. As described in further detail herein, implementations of the present disclosure address this challenge. For example, the electronic injection device can be configured to operate without a battery by using energy harvested from the environment. The components of the electronic injection device can be configured for low-power data processing and data transmission. An electronic injection device configured to operate without a battery has a low environmental footprint and can be manufactured as a disposable item.

Figure 1:
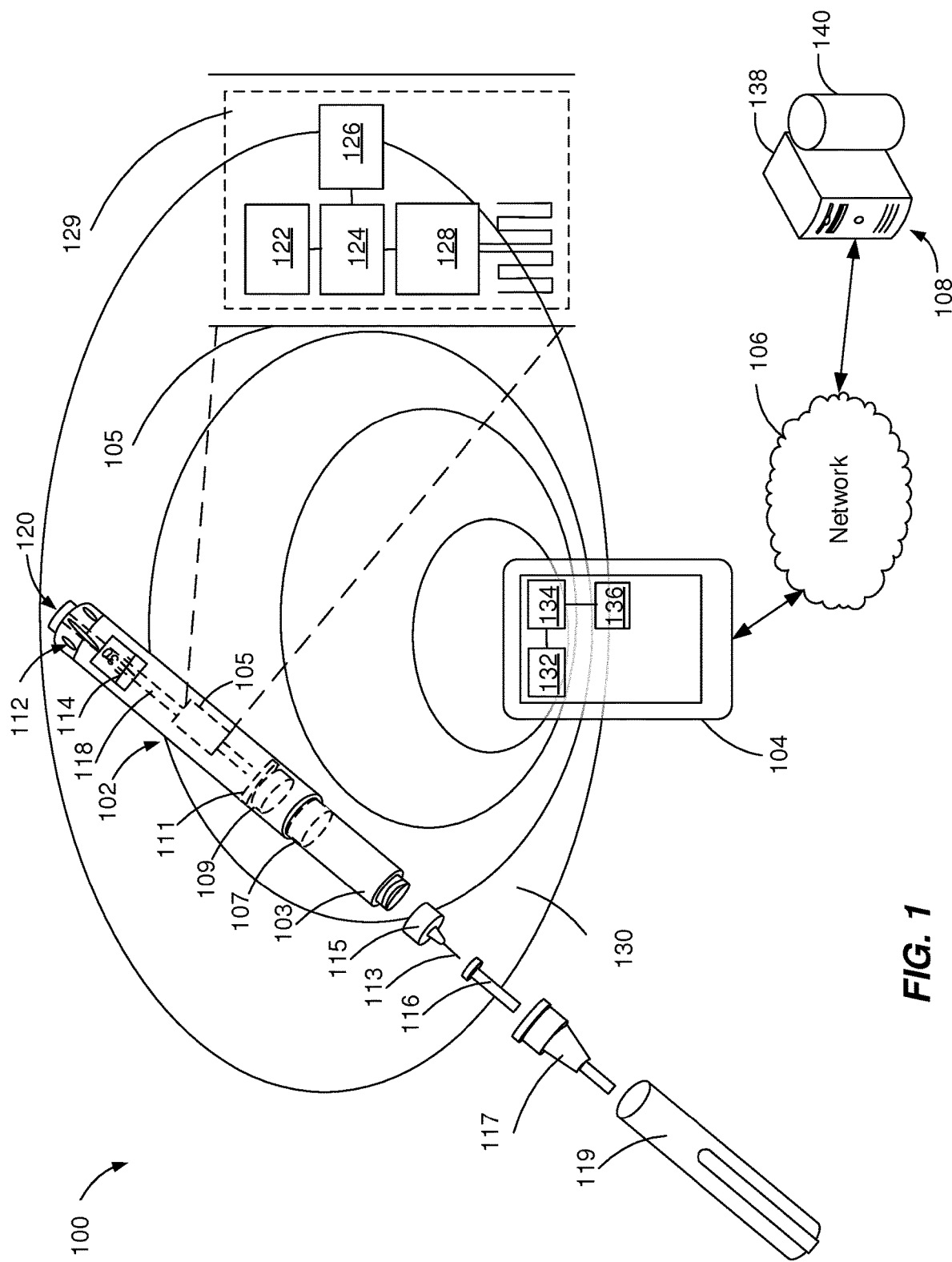
FIG. 1 is an exploded view of an example of a system in accordance with the present disclosure.

FIG. 1 illustrates an example system 100 that can be used to execute implementations of the present disclosure. For example, the example system 100 can be used for harvesting energy to power electronic components of one or more injection devices 102 to collect and transmit RF signals including injection device data. In the depicted example, the example system 100 includes an exploded view of the injection device 102, an external device 104, a network 106 and a server system 108.

The injection device 102 can be a pre-filled, disposable injection pen or the injection device 102 can be a reusable injection pen. The injection device 102 can be configured to communicate with the external device 104 (e.g., a smart phone configured to generate RF signals). For example, the injection device 102 can be configured to harvest energy from the external device 104 and to transmit injection device data to the external device 104. Energy harvesting is a technique in which the injection device 102 is wirelessly energized (e.g., charged) using the external device 104 as an energy distributor. The process of energy harvesting includes capturing RF signals generated by the external device 104, converting the RF signals to electric signals, boosting the electric signals to feed one or more components of the injection device with electric energy. The injection device 102 can transmit to the external device 104 operational data (e.g., date and time of start of usage of injection device 102 and sensor measurements) and corresponding treatment data (e.g., amount and time of medicament dispense by the injection device 102). In some implementations, the injection device 102 can be associated with an identifier that is used by the external device 104 to uniquely identify the injection device 102.

The injection device 102 can include a housing 110 and a needle assembly 115. The housing 110 can contain a medicament reservoir 103, an electronic module 105, a stopper 107, a plunger rod 118, a plunger head 109, a bearing 111, a dosage knob 112, a dosage window 114, and an injection button 120. The housing 110 can be molded from a medical grade plastic material such as a liquid crystal polymer cyclic olefin copolymer (COC), cyclo-olefin polymer (COP) or glass.

The medicament reservoir 103 can be configured to contain a fluid medicament. The medicament can include a pharmaceutical formulation containing at least one pharmaceutically active compound. The medicament can include insulin analogs, insulin derivatives, analgesics, hormones, beta agonists, corticosteroids, or a combination of any of the above-mentioned drugs. The medicament reservoir 103 can be a conventional, generally cylindrical, disposable container like a cartridge or a syringe used to package prepared fluids such as medicaments, anesthetics and the like. The medicament reservoir 103 can be provided with a pair of ends, one end having a pierceable membrane, which receives an inward end of needle 113 in a liquid tight sealing engagement and the other end being configured to be displaceable when dispensing the medicament.

A dose of the contained medicament can be ejected from the injection device 102 by turning the dosage knob 112, and the selected dose is then displayed via dosage window 114, for instance in multiples of so-called International Units (IU), wherein one IU is the biological equivalent of about 45.5 micrograms of pure crystalline medicament (1/22 mg). An example of a selected dose displayed in dosage window 114 may for instance be 30 IUs, as shown in FIG. 1. In some implementations, the selected dose can be displayed differently, for instance by an electronic display (e.g., the dosage window 114 may take the form of an electronic display). Turning the dosage knob 112 can cause a mechanical click sound to provide acoustical feedback to a user. The numbers displayed in dosage window 114 can be printed on a sleeve that is contained in housing 110 and mechanically interacts with a plunger head 109 that is fixed at the end of the plunger rod 118 and pushes the stopper 107 of the medicament reservoir 103. The bearing 111 can provide firm mounting to one or both ends of the plunger rod 118.

The plunger head 109 (e.g., a back end of the plunger) can be configured to expel a portion of the fluid by displacing the stopper 107 contained within the medicament reservoir 103, such that a position of the stopper 107 is associated with an amount of the fluid within the injection device 102. The stopper 107 can be a flexible stopper, such as a rubber stopper. The stopper 107 can be of a sufficient length so that the stopper 107 is not ripped or twisted when being engaged by the plunger head 109. The needle assembly 115 includes a needle 113 that can be affixed to the housing 110. The needle 113 can be covered by an inner needle cap 116 and an outer needle cap 117, which in turn can be covered by a cap 119. When needle 113 is stuck into a skin portion of a patient, and then injection button 120 is pushed, the medicament dose displayed in display window 114 can be ejected from injection device 102. When the needle 113 of injection device 102 remains for a certain time in the skin portion after the injection button 120 is pushed, a high percentage of the dose is actually injected into the patient's body. Ejection of the medicament dose can generate a mechanical click sound, which can be different from the sounds produced when using dosage knob 112.

Injection device 102 can be used for several injection processes until either medicament reservoir 103 is empty or the expiration date of injection device 102 (e.g., 28 days after the first use) is reached. Before using injection device 102 for the first time, it may be necessary to perform a priming operation to harvest energy from the external device 104 and/or to remove air from medicament reservoir 103 and needle 113. For instance, the priming operation can include selecting two units of medicament and pressing injection button 120 while holding injection device 102 with the needle 113 upwards. The impulse generated by selecting two units of medicament or pressing injection button 120 can initiate a communication between the electronic module 105 and the external device 104.

The electronic module 105 can be configured to perform and/or assist with one or more functions of the injection device 102 (e.g., the ejection of the medicament). The electronic module 105 can be molded within a component of the injection device 102 or attached to the injection device 102. The electronic module 105 can include a sensor 122, a control component 124, an energy module 126 and an antenna 128. The sensor 122 can be configured to detect a signal including an indication of medicament amount associated with a function of the injection device 102 and to generate a sensor signal based on the signal. The indication includes data representing the medicament amount. The function can include an operation of the injection device associated with dispensing a medicament amount, such as a displacement of the plunger rod 118. The signal including the indication of medicament amount can include an electric signal, an acoustic signal, a mechanical signal, and/or an optical signal. For example, the sensor 122 can be configured to generate an electric signal that is proportionate to an amount of medicament stored in the medicament reservoir 103 or dispensed by the injection device 102. Further, the sensor 122 can include a mechanical component, an acoustic component (e.g., a piezo element), an optical component (e.g., pairs of light emitting diodes and photodiodes), a magnetic component (e.g., permanent magnet or plastic containing ferromagnetic particles), an electric component (e.g., capacitive electrode, variable resistance), contact switches or a combination thereof. Further, the sensor 122 can include an incremental dosing sensor configured to measure an amount of expelled medicament. In some implementations, the sensor 122 can be configured to include in addition to the sensor configured to detect a signal indicating the amount of medicament an environmental sensor. The environmental sensor can include any of a temperature sensor, a humidity sensor, an air quality sensor, or a light intensity sensor. In some implementations, multiple sensors 122 can be included in the injection device 102 of FIG. 1 at different locations to detect medicament amount associated data and/or to increase an accuracy of a result associated with the sensor measurements. The sensor 122 can transmit a signal (e.g., a voltage) to the control component 124.

The control component 124 can be an ultra-low power (for example, in the μW to nW power range) platform chip. The control component 124 can be configured to retrieve energy from the energy module 126 and to process the signal received from the sensor 122 to transmit injection device data using the antenna 128. The antenna 128 can be a radio frequency (RF) antenna that can transmit injection device data to the external device 104. The antenna 128 can be electrically insulated from the surface of the injection device 128 to prevent a user interaction from influencing the signal and signal strength. The communication field 130 can enable communication between the injection device 102 and the external device 104. The communication field 130 can be based on an ultra-low power RF transmission protocol. The signals transmitted by the antenna 128 of the injection device 102 can include the amount of the fluid in the medicament reservoir 103, additional environmental values measured by the sensor 122, and the identifier of the injection device 102. In some implementations, the electronic components of the electronic module 105 can be integrated within a housing 129 at a single location or at multiple locations (e.g., fitted within or attached to the plunger rod 118, a cavity in the plunger head 109, a cavity in the stopper 107 or a wall of the medicament reservoir 103). The housing 129 can be a flexible carrier foil configured to be attached to a surface (e.g., curved portion) of an inner wall of the injection device 102 (e.g., a wall of the medicament reservoir 103). The housing 129 can be a hermetically closable box configured to be fitted within a cavity formed in a component of the injection device 102 (e.g., the plunger head 109 or the stopper 107). Further details regarding the components and functionalities of the electronic module 105 are provided with reference to FIG. 2.

The external device 104 can communicate with the injection device 102 over the communication field 130 and with one or more of the server devices 108 over the network 106. In some implementations, the external device 104 can include any appropriate type of computing device such as a desktop computer, a laptop computer, a handheld computer, a tablet computer, a personal digital assistant (PDA), a cellular telephone, a network appliance, a camera, a smart phone, a smart watch, an enhanced general packet radio service (EGPRS) mobile phone, a media player, a navigation device, an email device, a game console, or an appropriate combination of any two or more of these devices or other data processing devices.

The external device 104 can include a transceiver 132, a processor 134 and a display 136. The transceiver 132 can be configured to transmit signals to activate and/or powers the injection device 102 and receive signals from the injection device 102. The transceiver 132 can be configured to spontaneously transmit signals to the injection device 102 at a pre-set frequency during pre-set time intervals. The processor 134 can be configured to process the data transmitted by the injection device 102. The external device 104 can be configured to enable a user to interact with the display 136 (e.g., through a graphical user interface) to initiate a communication between the external device 102 and the injection device 102. The display 136 can be configured to display the data received from the injection device 102 and processed by the external processor 132.

In some implementations, the server device 108 includes at least one server 138 and at least one data store 140. In the example of FIG. 1, the server device 108 is intended to represent various forms of servers including, but not limited to a web server, an application server, a proxy server, a network server, and/or a server pool. In general, server systems accept requests for application services and provide such services to any number of client devices (e.g., the external device 104) over the network 106 to support monitoring of usage of the injection device 102. In some implementations, a user (such as a patient or a healthcare provider) can access the application services to analyze past and present data associated with the usage of the injection device 102. The past and present data associated with the usage of the injection device 102 can include dates of medicament injection, expelled doses per date and remaining amount of medicament within the injection device 102.

Figure 2:
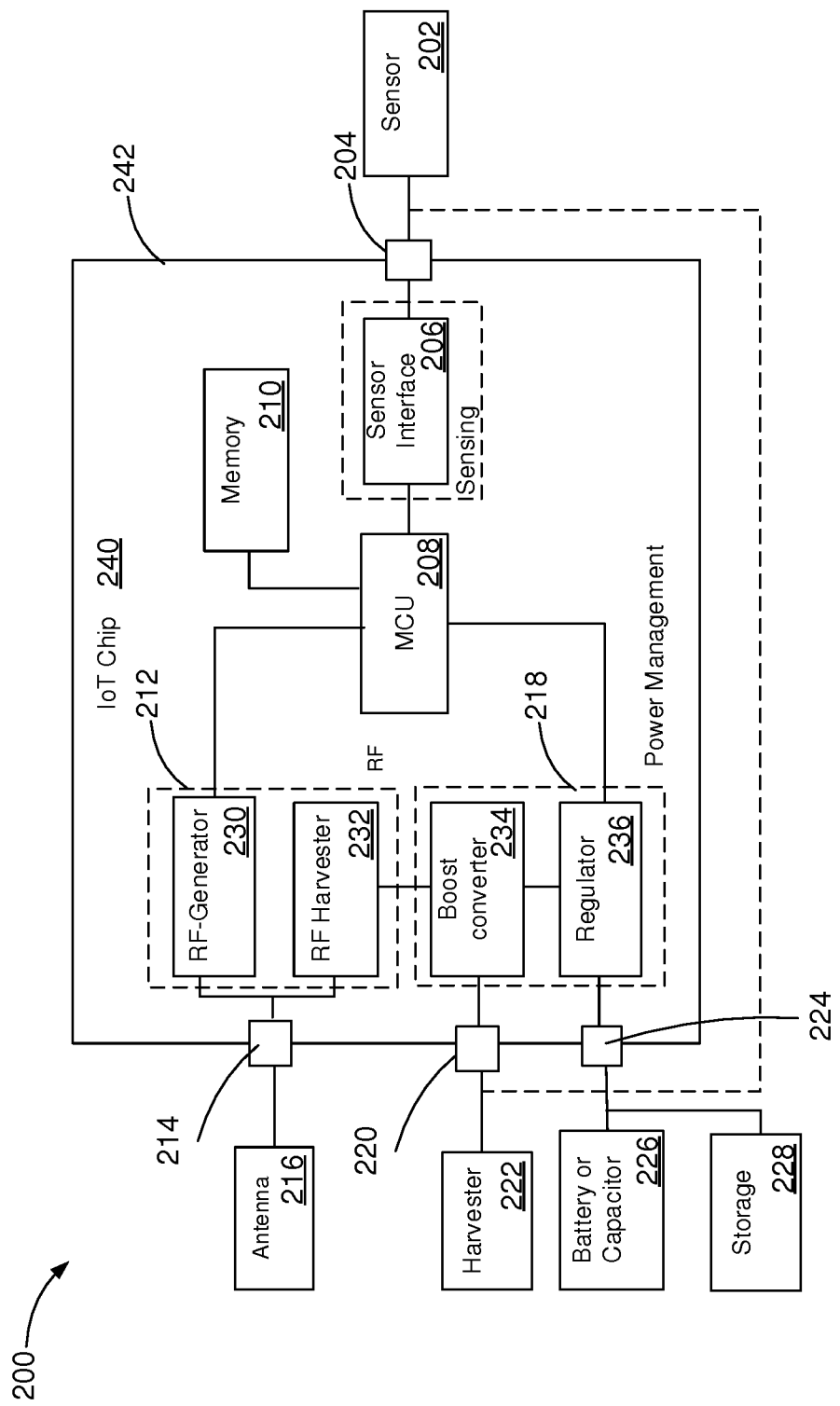
FIG. 2 is a block diagram of example system components that can execute implementations of the present disclosure.

FIG. 2 is a block diagram of an example electronic module 200 (e.g., electronic module 105 of FIG. 1) that can execute implementations of the present disclosure. The example electronic module 200 can be configured for ultra-low-power ($\mu$W) RF communication protocols. The example electronic module 200 includes a sensor 202, a sensor node 204, a sensor interface 206, a multipoint control unit (MCU) 208, a memory 210, an RF module 212, a communication node 214, an antenna 216, a power management module 218, an energy harvesting node 220, a harvester 222, an energy node 224, a battery 226 and a storage 228.

The sensor 202 can include the sensor 122, as described with reference to FIG. 1. The sensor 202 can include a plurality of sensors of the same type or of different types. A plurality of sensors of the same type can be used to increase an accuracy of a measurement and/or to measure a position dependent value. In some implementations, the sensor 202 (e.g., a dose sensor) triggers the activation of the electronic module 200. For example, an electrical contact can be detected by the sensor 202 to trigger the activation of the electronic module 200. In some implementations, the sensor 202 can be used as an energy harvester 222.

The sensor node 204 can be configured to collect signals from one or more sensors 202. In some implementations, the sensor node 204 can be a wireless sensor node (e.g., internet of things (IoT) edge node). The sensor interface 206 can be an analog to digital converter, a differential measurement bridge or a serial interface (e.g., an inter-integrated circuit, a serial peripheral interface, a universal asynchronous receiver transmitter, a universal synchronous/asynchronous receiver transmitter, a transistor-transistor logic or other protocol interfaces). The sensor interface 206 can be configured to transmit the collected signals to the MCU 208.

The MCU 208 can be a control component defining a junction point of the electronic module 200 that provides the capability for three or more terminals and gateways to transfer signals between each other. The MCU can be an integrated circuit (IC) on the IoT Chip 240. The MCU 208 can process one or more signals received from the other electronic components of the electronic module 200 (e.g., sensor interface 206, memory 210, and RF module 212). The MCU 208 can trigger a measurement of the sensor 202. The MCU 208 can transmit a signal to the RF module 212 to trigger a transmission of data to an external device.

The memory 210 can include a microcontroller, a microprocessor or a combination of microprocessor components and other components formed in a single package. The memory 210 can be an arithmetic and/or a logic unit array. For example, the memory 210 can be configured to execute operations on sensor data to generate output data, as described in detail with reference to FIG. 3. The memory 210 can be configured for low power consumption such that it can operate using the energy supplied by the power management module 218. For example, the memory 210 can include one or more of an electrically erasable programmable read-only memory (EEPROM), static random access memory (SRAM), Ferroelectric Random Access Memory (FRAM), Magnetoresistive RAM (MRAM), and phase change memory (PCM). FRAM is a non-volatile random-access memory, which is based on the integration of a ferroelectric material to achieve non-volatility. FRAM does not require a special sequence to write data nor does it require a charge pump to achieve the higher programming voltages (e.g., FRAM programs at I 0.5V). FRAM has the advantage of low power consumption (e.g., lower than EEPROM), low write voltage requirements, fast write speeds and a large number of write-erase cycles. FRAM is compatible to standard CMOS processes, which means that it can be integrated with other logic functions into the electronic module 200, by implementing additional processing steps. MRAM provides fast read/write speeds in the order of approximately 35 ns, long data retention and an unlimited number of read/write cycles. Reads of MRAM are not destructive.

The RF module 212 is a transceiver configured to enable communication with an external device over the communication node 214 and the antenna 216 using ultra-low power RF. The RF module 212 includes a RF generator 230 and a RF harvester 232. The RF generator 230 can be configured to generate RF signals based on electric signals received from the MCU 208 and send the RF signals to the antenna 216. The RF harvester 232 can be configured for harvesting energy from the RF signals generated by an external device, received by the antenna 216 and integrated by the communication node 214. The RF harvester 232 can include a piezoelectric crystal that generates an electrical pulse in response to receiving RF signals. The communication node 214 can be configured to enable communication through one or more antennas 216 by integrating signals received from the antennas 216.

The antenna 216 can be designed fora specific frequency together with a matching network. A plurality of antennas 216 can be included in the electronic module 200 to increase the bandwidth of communication (e.g., to enable communication between the electronic module 200 and multiple types of external devices). In addition to the antenna 216 and the RF harvester 232, the electronic module 200 can include one or more harvesters 222. The harvesters 222 are connected to the boost converter 234 through the energy-harvesting node 220. The one or more harvesters 222 can be configured for harvesting energy from the electromagnetic field generated by an external device. The one or more harvesters 222 can include a moving magnet that induces a current in a coil, a piezo crystal that generates an electrical pulse or a charge pump that accumulates electrical charge. The energy harvesters 222 can have a range of output voltages (e.g., from 0.1 to 2 Volts) that can be similar or different from the voltage range output by the RF module 212. In some implementations, the energy harvesters 222 are in direct communication with the sensor 202 to trigger an activation of an energy harvest or a sensor measurement. The RF harvester 232 and the energy harvesters 222 can transmit the generated energy supply to the power management module 218.

The power management module 218 can be configured to manage power for the electronic module 200 and can be responsible for enabling or disabling the consuming circuit, depending on the available energy level. The power management module 218 includes a boost converter 234 and a regulator 236. The boost converter 234 can be configured to increase the voltage level for use in the electronic module 200. The boost converter 234 can be a DC/DC boost converter. The regulator 236 can manage the storage of the harvested energy and regulates the DC supply voltages for the MCU 208 in a power range from tens of µW to hundreds mW with sub-µW operation losses. In some implementations, the regulator 236 can be temporarily shut down by MCU 208, during transmission of RF signals from the electronic module 200 using the RF generator 230.

The power management module 218 can include a power path management for an optional backup rechargeable battery or capacitor 226 connected through the energy node 224. The rechargeable battery or capacitor 226 can include a programmable voltage monitor to support charging and prevent overcharging or overdischarging. The rechargeable battery or capacitor 226 can serve as a short-term storage for the harvested energy. The rechargeable battery or capacitor 226 can be configured to supply energy to the electronic module 200 while no external device is available to generate a RF communication field. In some implementations, the energy harvester 222 can reduce the size of or replace the battery or capacitor 226. For example, the electronic module 200 does not include a rechargeable battery or capacitor 226 and the power source for the electronic module 200 is limited to the RF communication field. The power management module 218 can optionally include an intermediate energy storage 228. The intermediate energy storage 228 can be configured to supply power to the electronic module 200 during consumption peaks.

In some implementations, the sensor interface 206, the MCU 208, the memory 210, the RF module 212 and the power management module 218 are integrated in an internet of things (IoT) platform chip 240. The IoT chip 240 is an electronics package such as an SOC (system on a chip). The IoT platform chip 240 provides an ultra-low power RF transmission protocol. The IoT 240 can be configured such that it includes a plurality of wireless nodes (e.g., the sensor node 204, the communication node 214, the energy-harvesting node 220 and the energy node 224) to communicate with the remaining components of the electronic module 200. In some implementations, the IoT platform chip 240 includes a housing 242 (e.g., housing 129 in FIG. 1) that can be attached to an injection device. The housing 242 can be configured to support and/or embed all the components of the IoT platform chip 240 (e.g., the sensor interface 206, the MCU 208, the memory 210, the RF module 212, the power management module 218 and the nodes 204, 214, 220, 224). In some implementations, the antenna 216 is integrated in the IoT platform chip 240, which is attached near to a surface of an injection device to prevent attenuation of the signals transmitted and received by the antenna 216. The frequency spectrum of the IoT platform chip 240 enable the use of a relatively small antenna 216 (e.g., with a width of a few millimeters). The IoT platform chip 240 can have a base frequency higher than 1 GHz to minimize the size of the antenna 216 to be smaller than 12 mm×12 mm.

Figure 3:
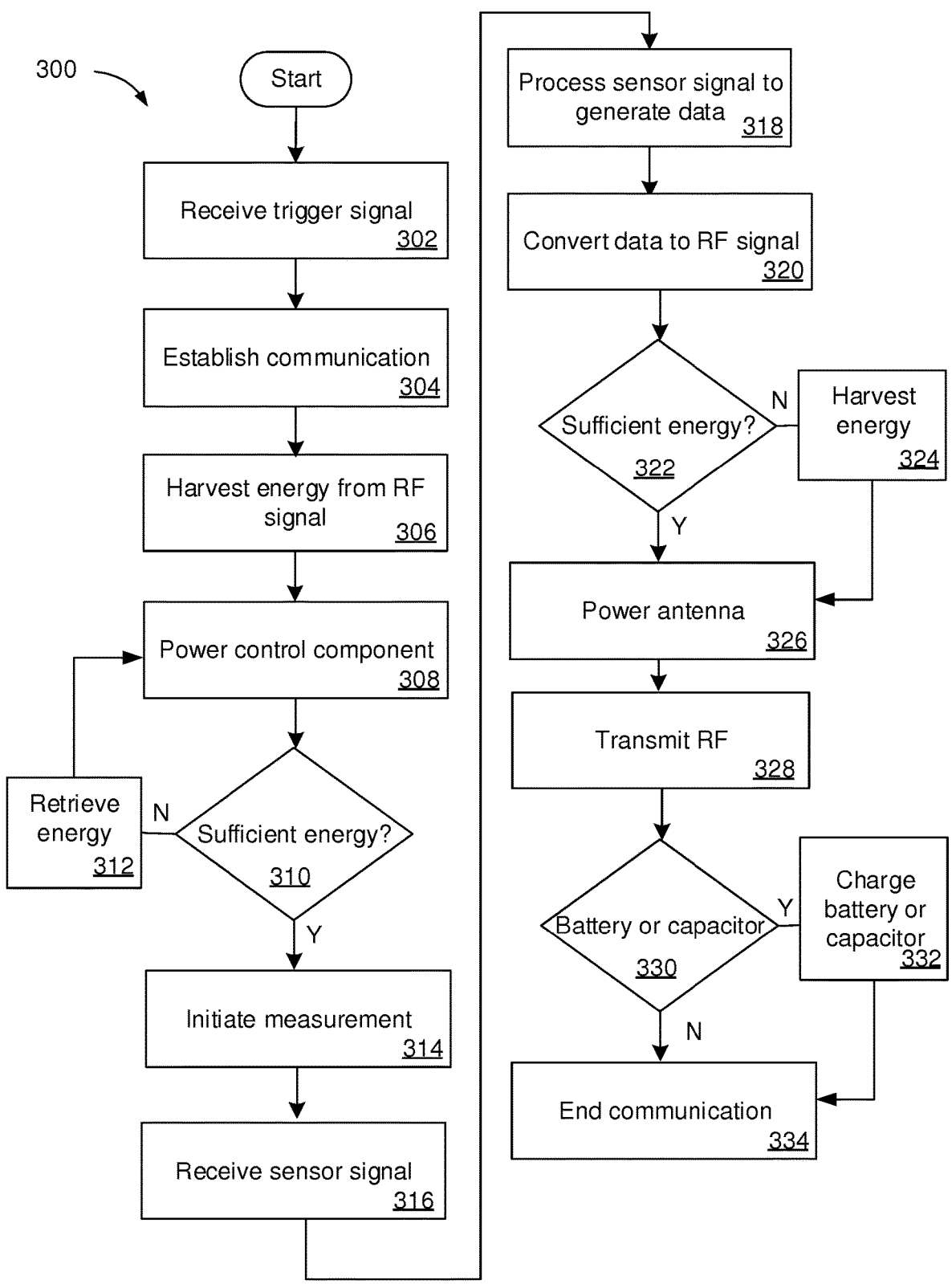
FIG. 3 is a flowchart illustrating an example process that can be executed to perform operations of the present disclosure.

FIG. 3 is a flowchart illustrating an example process 300 that can be executed by devices and systems described with reference to FIGS. 1 and 2. The process 300 begins by receiving a trigger signal (302). The trigger signal can include a priming operation on an injection device having no internal energy source or a limited energy source. The priming operation can be initiated by a user of the injection device. An example of a priming operation performed with the injection device can include selecting a particular number (e.g., one or two) of units of medicament and pressing an injection button while holding the injection device with the needle upwards. Another example of a priming operation performed with the injection device can include pressing a priming button of the injection device configured as an electric switch. In some implementations, the trigger signal can include an interrogation signal generated by an external device. The interrogation signals include electromagnetic (e.g., RF) waves that are broadcasted by the external device to detect the presence of the injection device within a communication range. The interrogation signal can be automatically generated by the external device based on one or more conditions. The conditions can include a transmission frequency, a transmission time and/or a time interval. For example, a medicament treatment can be scheduled to be performed within a particular time interval, during which the external device can generate interrogation signals at a given frequency. The signal can be generated by the external device in response to a user input on the external device. For example, a user can interact with an external device to initiate a medicament dispensing service. The trigger signal can include at least one of a mechanical signal, an acoustic signal and a RF signal.

If the distance between the injection device and the external device is within the communication range, in response to receiving the trigger signal a communication is established between the injection device and the external device (304). During established communication, the injection device can be configured to harvest energy from the interrogation signals transmitted by the external device (306). Harvesting energy can include generating, by a RF harvester, an electric signal based on the RF signal received by an antenna of the injection device. In some implementations, the harvested energy is boosted for voltage increase. The electrical energy is used to power a control component (308). The control component can determine whether the received electric energy is sufficient to activate one or more additional components of the injection device (310). If it is determined that additional energy is necessary, supplemental energy can be retrieved from one or more of a rechargeable battery, a capacitor and an energy harvester (312). Retrieving the supplemental energy can include harvesting energy from additional sources different from the RF signal. The supplemental energy can be combined with the RF generated energy and directed towards the control component.

In response to determining that the energy is sufficient, one or more additional components of the injection device are activated to initiate sensor measurement (314). Sensor measurements can include detection of an indication associated with a function of the injection device to generate a sensor signal. The indication can include a mechanical signal, an acoustic signal, an optical signal, a magnetic signal, an electric signal, or a combination thereof generated before, during or after the function of the device. The function of the injection device can include a movement of the plunger rod, a displacement of the plunger head, a dose selection or other operations associated with dispensing of the medicament. The indication can be converted by a sensor into a sensor signal. The control component can be configured to receive the sensor signal generated by the sensor (316). The control component can process the sensor signal to generate injection device data (318). The injection device data can include sensor signals from a plurality of sensors and additionally stored data. For example, the injection device data can include a unique identifier for the injection device, an amount of administered medicament, an amount of medicament within a cartridge and/or injection device, a medicament temperature, a timestamp of administering the medicament, a location, and/or a situation specific data for the injection device.

The injection device data can be transmitted to an RF generator to convert the data to a RF signal (320). It is determined whether the injection device has sufficient energy to power the antenna to transmit the RF signal associated with the injection device data to the external device. If it is determined that additional energy is necessary, supplemental energy can be retrieved from one or more of the rechargeable battery, the capacitor and the energy harvester (324). If it is determined that the antenna has sufficient energy, the antenna is powered (326) and the RF signal is transmitted to the external device (328). In some implementations, in response to successful transmission of RF signal, the injection device, if it includes a battery or a capacitor, can determine if the included battery or capacitor store sufficient energy (330). If the included battery or capacitor does not store sufficient energy the communication field is maintained with the external device to charge the included battery or capacitor (332). If the injection device does not include a battery or a capacitor or if the included battery or capacitor store sufficient energy, the communication between the injection device and the external device can be terminated.

Figure 4:
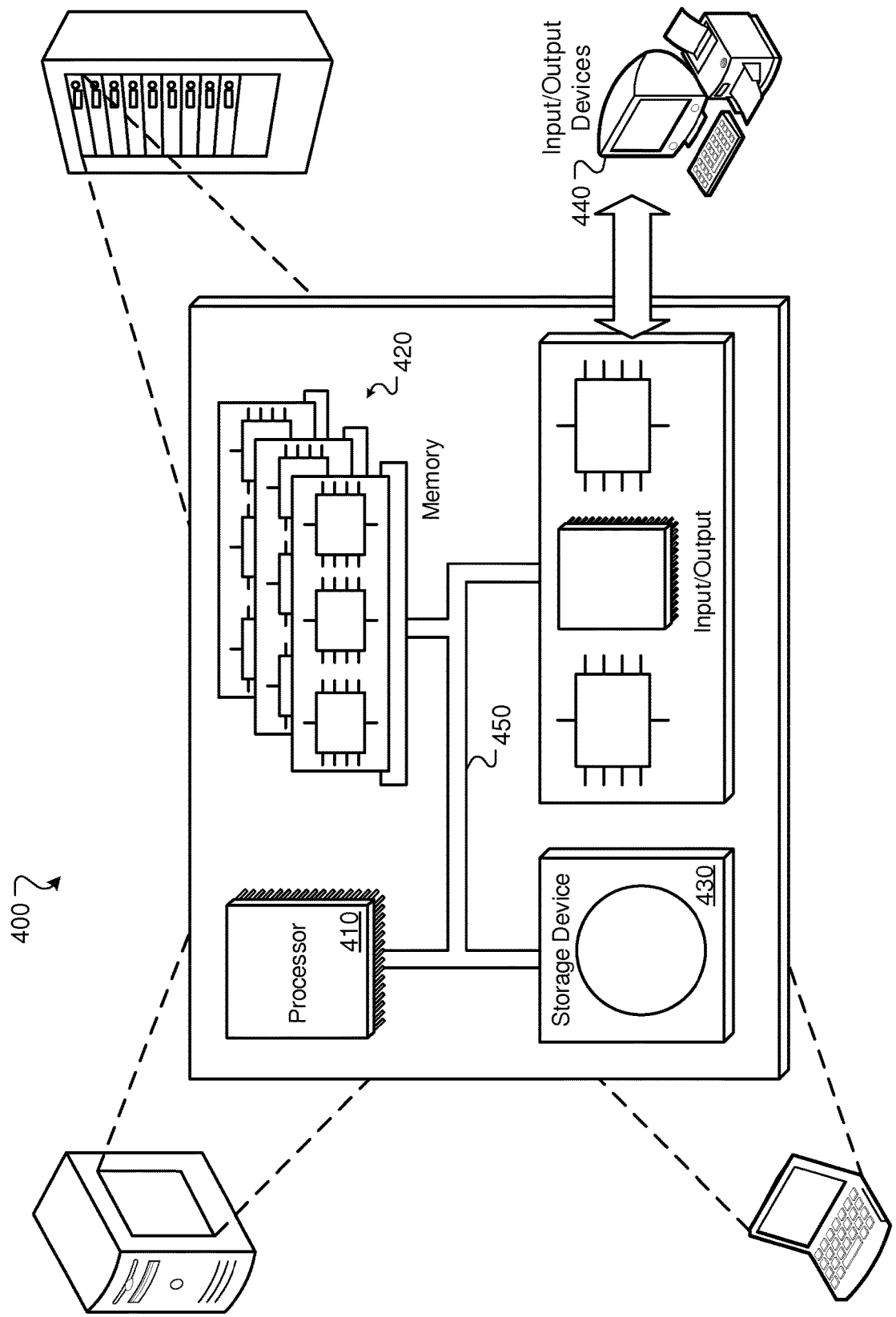
FIG. 4 is a schematic illustration of example computer systems that can be used to execute implementations of the present disclosure.

FIG. 4 shows a schematic diagram of an example computing system 400. The system 400 can be used for the operations described in association with the implementations described herein. For example, the system 400 may be included in any or all of the server components discussed herein. The system 400 includes a processor 410, a memory 420, a storage device 430, and an input/output device 440. Each of the components 410, 420, 430, and 440 are interconnected using a system bus 450. The processor 410 is capable of processing instructions for execution within the system 400. In one implementation, the processor 410 is a single-threaded processor. In another implementation, the processor 410 is a multi-threaded processor. The processor 410 is capable of processing instructions stored in the memory 420 or on the storage device 430 to display graphical information for a user interface on the input/output device 440.

The memory 420 stores information within the system 400. In one implementation, the memory 420 is a computer-readable medium. In one implementation, the memory 420 is a volatile memory unit. In another implementation, the memory 420 is a non-volatile memory unit. The storage device 430 is capable of providing mass storage for the system 400. In one implementation, the storage device 430 is a computer-readable medium. In various different implementations, the storage device 430 may be a floppy disk device, a hard disk device, an optical disk device, or a tape device. The input/output device 440 provides input/output operations for the system 400. In one implementation, the input/output device 440 includes a keyboard and/or pointing device. In another implementation, the input/output device 440 includes a display unit for displaying graphical user interfaces that enable a user to access data related to an item that is collected, stored and queried as described with reference to FIGS. 1-3.

The features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body. The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin. Examples of insulin derivatives are, for example, B29-N-myristoyl-des(B30) human insulin, Lys(B29) (N-tetradecanoyl)-des(B30) human insulin (insulin detemir, Levemir®), B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

A number of implementations of the present disclosure have been described. Nevertheless, it will be understood that various modifications may be made without departing from the spirit and scope of the present disclosure. Accordingly, other implementations are within the scope of the following claims.

The invention claimed is:

1. A module for attachment to an injection device, the module comprising:
   a housing attached to a surface of the injection device;
   a sensor attached to the housing, the sensor being configured to detect a signal associated with an amount of medicament within the injection device and to generate a sensor signal based on the signal;
   a control component coupled to the sensor, the control component being configured to harvest energy to process the sensor signal and to generate injection device data, wherein the control component comprises an energy harvester configured to harvest the energy in response to receiving a trigger signal, the trigger signal including a priming operation of the injection device and an interrogation signal; and
   an antenna coupled to the control component and configured to transmit a radio frequency (RF) signal based on the injection device data.

2. The module of claim 1, comprising a transceiver configured to enable the transmission of the injection device data from the control component to the antenna.

3. The module of claim 1, wherein the priming operation of the injection device comprises a displacement of one of a push button, a plunger head or a plunger rod of the injection device.

4. The module of claim 1, wherein the control component comprises a boost converter configured to increase a voltage level of an energy supplied by the energy harvester.

5. The module of claim 4, comprising an integrated voltage regulator configured to regulate the voltage level generated by the boost converter.

6. The module of claim 1, wherein the sensor comprises at least one of a temperature sensor, a humidity sensor, or a fill level sensor.

7. The module of claim 1, wherein the sensor is configured to generate the sensor signal using ultra-low power.

8. The module of claim 7, wherein the ultra-low power is in a range from about 50 nW to about 1 µW.

9. The module of claim 1, wherein the control component is configured to:
   determine whether the harvested energy is sufficient to activate one or more additional components of the module, and
   if it is determined that the harvested energy is insufficient to activate the one or more additional components, retrieve supplemental energy from at least one of a rechargeable battery, a capacitor, or an intermediate energy storage.

10. An injection device comprising:
   a sensor configured to detect a signal associated with an amount of medicament within the injection device and to generate a sensor signal based on the signal;
   a control component electrically coupled to the sensor, the control component being configured to harvest energy to process the sensor signal and to generate injection device data, wherein the control component comprises an energy harvester configured to harvest the energy in response to receiving a trigger signal, the trigger signal including a priming operation of the injection device and an interrogation signal; and
   an antenna electrically coupled to the control component and configured to transmit a radio frequency (RF) signal based on the injection device data.

11. The injection device of claim 10, comprising a transceiver configured to enable the transmission of the injection device data from the control component to the antenna.

12. The injection device of claim 10, wherein the control component is configured to:
   determine whether the harvested energy is sufficient to activate one or more additional components of the injection device, and
   if it is determined that the harvested energy is insufficient to activate the one or more additional components, retrieve supplemental energy from at least one of a rechargeable battery, a capacitor, or an intermediate energy storage.

13. The injection device of claim 10, wherein the priming operation of the injection device comprises a displacement of one of a push button or a piston of the injection device.

14. The injection device of claim 10, wherein the control component comprises a boost converter configured to increase a voltage level of an energy supplied by the energy harvester.

15. A medicament injection system comprising:
   an injection device comprising:
      a sensor configured to detect a signal associated with an amount of medicament within the injection device and to generate a sensor signal based on the signal;
      a control component electrically coupled to the sensor, the control component being configured to harvest energy to process the sensor signal and to generate injection device data, wherein the control component comprises an energy harvester configured to harvest the energy in response to receiving a trigger signal, the trigger signal including a priming operation of the injection device and an interrogation signal; and
      an antenna electrically coupled to the control component and configured to transmit a radio frequency (RF) signal based on the injection device data; and
   a computing device configured to receive the RF signal transmitted by the antenna.

16. The medicament injection system of claim 15, wherein the injection device further comprises a transceiver configured to enable the transmission of the injection device data from the control component to the antenna.

17. The medicament injection system of claim 15, wherein the control component is configured to:
   determine whether the harvested energy is sufficient to activate one or more additional components of the injection device, and
   if it is determined that the harvested energy is insufficient to activate the one or more additional components, retrieve supplemental energy from at least one of a rechargeable battery, a capacitor, or an intermediate energy storage.

18. The medication injection system of claim 15, wherein the priming operation of the injection device comprises a displacement of one of a push button or a piston of the injection device.

19. The medication injection system of claim 15, wherein the control component comprises a boost converter configured to increase a voltage level of an energy supplied by the energy harvester.

20. The medication injection system of claim 19, wherein the injection device further comprise an integrated voltage regulator configured to regulate the voltage level generated by the boost converter.

* * * * *